(12) United States Patent
Mizrahi

(10) Patent No.: US 7,125,417 B2
(45) Date of Patent: Oct. 24, 2006

(54) AROMATHERAPY HERB PACK

(76) Inventor: Hagay Mizrahi, 4551 Larkwood Ave., Woodland Hills, CA (US) 91364

( * ) Notice: Subject to any disclaimer, the term of this patent is extended or adjusted under 35 U.S.C. 154(b) by 90 days.

(21) Appl. No.: 10/923,521

(22) Filed: Aug. 20, 2004

(65) Prior Publication Data

US 2006/0041235 A1 Feb. 23, 2006

(51) Int. Cl.
*A61F 7/00* (2006.01)
*A61F 13/00* (2006.01)

(52) U.S. Cl. .................. 607/114; 604/308; 607/109

(58) Field of Classification Search .............. 604/289, 604/291, 308; 607/109, 114, 96; 424/733, 424/739
See application file for complete search history.

(56) References Cited

U.S. PATENT DOCUMENTS

| | | | | |
|---|---|---|---|---|
| 2,071,706 A | * | 2/1937 | Reach | 607/112 |
| 3,839,621 A | * | 10/1974 | Hariu | 219/211 |
| 4,061,897 A | * | 12/1977 | Thykeson | 219/211 |
| 4,742,827 A | | 5/1988 | Lipton | |
| 4,752,971 A | * | 6/1988 | Meserol | 2/88 |
| 4,886,063 A | * | 12/1989 | Crews | 607/112 |
| D336,958 S | * | 6/1993 | Pryor | D24/206 |
| 5,300,104 A | | 4/1994 | Gaudreault et al. | |
| 5,443,488 A | * | 8/1995 | Namenye et al. | 607/104 |
| 5,476,492 A | | 12/1995 | Unrug | |
| 5,603,727 A | | 2/1997 | Clark et al. | |
| 5,697,963 A | * | 12/1997 | Augustine | 607/108 |
| D401,800 S | * | 12/1998 | Rosenstadt et al. | D6/598 |
| 5,890,487 A | | 4/1999 | Kimmel | |
| 5,948,010 A | | 9/1999 | Adamec | |
| 5,984,953 A | | 11/1999 | Sabin et al. | |
| 6,019,782 A | * | 2/2000 | Davis et al. | 607/96 |
| 6,099,555 A | | 8/2000 | Sabin | |
| 6,123,946 A | * | 9/2000 | Wei | 424/750 |
| 6,173,675 B1 | | 1/2001 | Licciardo | |
| 6,185,744 B1 | * | 2/2001 | Poholski | 2/102 |
| 6,699,271 B1 | | 3/2004 | Clayton | |
| 6,972,029 B1 | * | 12/2005 | Mayrhofer et al. | 607/114 |
| 2001/0047544 A1 | * | 12/2001 | Catalano-Carriveau | 5/490 |
| 2002/0042641 A1 | * | 4/2002 | Johnson | 607/114 |
| 2002/0198580 A1 | * | 12/2002 | Clayton | 607/109 |
| 2003/0115670 A1 | * | 6/2003 | Antinoro | 5/420 |
| 2004/0088030 A1 | * | 5/2004 | Jung, Jr. | 607/109 |

\* cited by examiner

*Primary Examiner*—Tatyana Zalukaeva
*Assistant Examiner*—Paula L. Craig
(74) *Attorney, Agent, or Firm*—David A. Belasco; Belasco Jacobs & Townsley, LLP

(57) ABSTRACT

An aromatherapy herb pack has a flexible, aroma-permeable cover having upper and lower layers joined at their outer edges to form an interior space to contain thermal reservoir and aromatherapy materials. The interior space is divided into a series of subspaces in the form of parallel, tube-shaped containers to prevent shifting of the contained materials. A central opening is provided penetrating the upper and layers of the cover. The opening permits a user to place the herb pack over his head and onto his shoulders. The opening is X-shaped to permit maximum shoulder contact. The openings are circular in another embodiment, designed to fit snugly about a user's neck. A slit is provided extending from the outer edge of the herb pack to the opening for easy placement about the neck. A fastener, such as a hook and loop, button, zipper or tie string is used to close the slit.

14 Claims, 3 Drawing Sheets

AROMATHERAPY HERB PACK

FIELD OF INVENTION

The invention pertains to devices for alleviating muscle soreness, fatigue and stress. More particularly, the invention relates to herb packs that can be heated or cooled and then applied to the body to provide relief through temperature difference and aromatherapy related to the herbs contained in a wearable pad.

BACKGROUND OF THE INVENTION

Heating and cooling pads have long been in use for alleviating soreness, stiffness, aching muscles and the results of various types of injuries. Likewise, aromatherapy products have been in use in Eastern cultures for hundreds of years and are now achieving prominence in the West. The combination of heating and cooling devices with aromatherapy products has served to provide increased benefits for those with muscle, tendon and joint problems. A number of inventions have been developed that use one or more of these components to alleviate pain or soreness.

U.S. Pat. No. 6,699,271, issued to Clayton, describes a therapeutic wrap designed to be applied to various portions of an individual, such as the neck and shoulders. The wrap contains a plurality of narrow channels into which a filler material, such as Basmati rice, is provided. Various herbs such as chamomile or lavender are also provided within each of the channels to allow for aromatherapy. The rice serves as heat-transferring material. Each channel is separated from its adjoining channel by stitching it closed such. The neck wrap is designed to encircle the neck of the user and fasten with Velcro fasteners. The Velcro fasteners and the use of narrow channels keep the filler material within the wrap from shifting and hold it close to the neck during treatment. Basmati rice and aromatic herbs are the preferred fillers. In use, the wrap is heated by placing it in a conventional oven, crockpot or microwave, or cooled by placing it into a freezer or refrigerator.

U.S. Pat. No. 5,476,492, issued to Unrug, discloses a body warmer for therapeutic purposes containing whole herb seed. The body warmer is comprised of a shell of an elastic breathable and pliable material, divided into chambers containing rebufacient herbal material in the form of whole seed grains, and means of attachment to keep the warmer in place in a desired area of the human body. The shell is made in two layers of fabric fastened along two long sides at side seams. Other seams divide the shell into a number of tubular chambers filled with herb seed. Ribbon tie straps attached to corners of the shell are used to fasten the shoulder warmer pad to the body.

U.S. Pat. No. 5,603,727, issued to Clark et al., is directed to a thermal pack having temperature-retaining particles within the packet. A plurality of barriers located within the packet form migration paths and retaining areas. The pack that has pliable container consisting of top and bottom surfaces connected about their periphery. Barriers within the compartment to direct the migration of the heat retaining particles in the compartment are formed by sewing portions of the top and bottom surfaces together in a chevron shape. Heat retaining particles are preferably re-cleaned animal feed corn, which can be scented. The thermal material can be either heated or cooled depending on the appropriate treatment.

U.S. Pat. No. 5,948,010, issued to Adamee, discloses a therapeutic heat application device. The device comprises a pad portion having a wide central portion divided into a plurality of narrow sections by vertically extending seams. Each of the tapered side portions are divided into two sections by a horizontally extending seam. The sections of the central portion and side portions are filled with a granular natural filler material where the seams would maintain the proper positioning of the filler material throughout the pad portion. A pair of straps have hook and loop fasteners for fastening the pad around the body of the wearer. In use, the device would be heated in a microwave oven or chilled for cold therapy.

U.S. Pat. No. 5,890,487, issued to Kimmel, is directed to a flat fabric bag that holds a quantity of dried Indian corn, which can be scented. The bag can then be heated in a microwave oven or cooled in a freezer. The heating pad that is formed by sewing two pieces of cloth together to form closed bag which is then filled with corn. To keep the corn spread throughout the bag, a number of baffle stitches are used which divide the bag into sections that hold a uniform quantity of corn. The bag is used primarily over the shoulders, where the wide end portions drape over the tops of the shoulders and the long center portion runs along the upper back or neck.

It is an objective of the present invention to provide a means to provide a means to alleviate muscle soreness, cramps, aches and pains, etc. without the use of drugs or invasive procedures. It is a further objective to provide a pad that provides these benefits that can be comfortably and easily worn by a user. It is a still further objective of the invention to provide a pad that can provide both heating and cooling to the body. It is yet a further objective to provide a pad that includes the benefits of aromatherapy for the user. Finally, it is an objective of the invention to provide a pad with the above benefits that is easily attached and removed.

While some of the objectives of the present invention are disclosed in the prior art, none of the inventions found include all of the requirements identified.

SUMMARY OF THE INVENTION

The present invention addresses all of the deficiencies of heating and cooling pack inventions and satisfies all of the objectives described above.

(1) An aromatherapy herb pack providing the desired features may be constructed from the following components. A flexible, aroma-permeable cover is provided. The cover has an upper layer and a lower layer. The upper and lower layers are joined at their outer edges. The joined layers define a space between them. The space is divided into a plurality of subspaces. An opening is provided. The opening is centrally located in the cover and penetrates the upper and lower layers. The opening is sized and shaped to permit the cover to be placed over the head of a user. A quantity of thermal reservoir material is provided. A quantity of aromatherapy material is provided. The thermal material and the aromatherapy material are secured within the subspaces. When the herb pack is heated or cooled it is placed over the head and about the shoulders, chest and back of the user, thereby heating or cooling the user while providing aromatherapy benefits.

(2) In a variant of the invention, the subspaces are a series of tube-shaped containers.

(3) In another variant, the tube-shaped containers are divided into substantially equal portions to prevent shifting of the thermal material and the aromatherapy material.

(4) In still another variant, the opening is X-shaped, thereby permitting maximum contact of the herb pack with the user while permitting the herb pack to be placed over the user's head.

(5) In yet another variant, one end of the X-shaped opening extends to one of the outer edges of the cover, thereby permitting the herb pack to be easily placed about the wearer's neck.

(6) In a further variant, a fastener is provided. The fastener closes the open end of the X-shaped opening that extends to one of the outer edges of the cover.

(7) In still a further variant, the fastener is selected from the group consisting of buttons, hook and loop fasteners, zippers and tie strings.

(8) In yet a further variant, the opening is sized and shaped to fit snugly about the neck of the user and further includes a slit. The slit extends from an edge of the opening to one of the outer edges of the herb pack.

(9) In another variant of the invention, a fastener is provided. The fastener closes the slit.

(10) In still another variant, the fastener is selected from the group consisting of buttons, hook and loop fasteners, zippers and tie strings.

(11) In yet another variant, the thermal reservoir materials are selected from the group consisting of corn, rice, wheat, oats, barley, beans and flaxseed.

(12) In a further variant, the aromatherapy materials are selected from the group consisting of cinnamon, chamomile, lemongrass, peppermint, rosemary, spearmint, valerian root, white willow, yarrow, lavender ginger and yellow dock root.

(13) In still a further variant, the subspaces are closed with stitching.

(14) In yet a further variant, the subspaces have openable closures to permit introduction of alternative thermal and aromatherapy materials.

(15) In a final variant, the openable closures are selected from the group consisting of hook and loop fasteners, zippers, buttons and tie strings.

An appreciation of the other aims and objectives of the present invention and an understanding of it may be achieved by referring to the accompanying drawings and the detailed description of a preferred embodiment.

DESCRIPTION OF THE DRAWINGS

DETAILED DESCRIPTION OF THE PREFERRED EMBODIMENT (1) FIGS. 1–6 illustrate an aromatherapy herb pack 10 providing the desired features that may be constructed from the following components. A flexible, aroma-permeable cover 15 is provided. The cover 15 has an upper layer 20 and a lower layer 25. The upper 20 and lower 25 layers are joined at their outer edges 30. The joined layers 20, 25 define a space 35 between them. The space 35 is divided into a plurality of subspaces 40. An opening 45 is provided. The opening 45 is centrally located in the cover 15 and penetrates the upper 20 and lower 25 layers. The opening 45 is sized and shaped to permit the cover 15 to be placed over the head 50 of a user 55. A quantity of thermal reservoir material 60 is provided. A quantity of aromatherapy material 65 is provided. The thermal material 60 and the aromatherapy material 65 are secured within the subspaces 40. When the herb pack 10 is heated or cooled it is placed over the head 50 and about the shoulders 65, chest 70 and back 75 of the user 55, thereby heating or cooling the user 55 while providing aromatherapy benefits.

Figure 1:
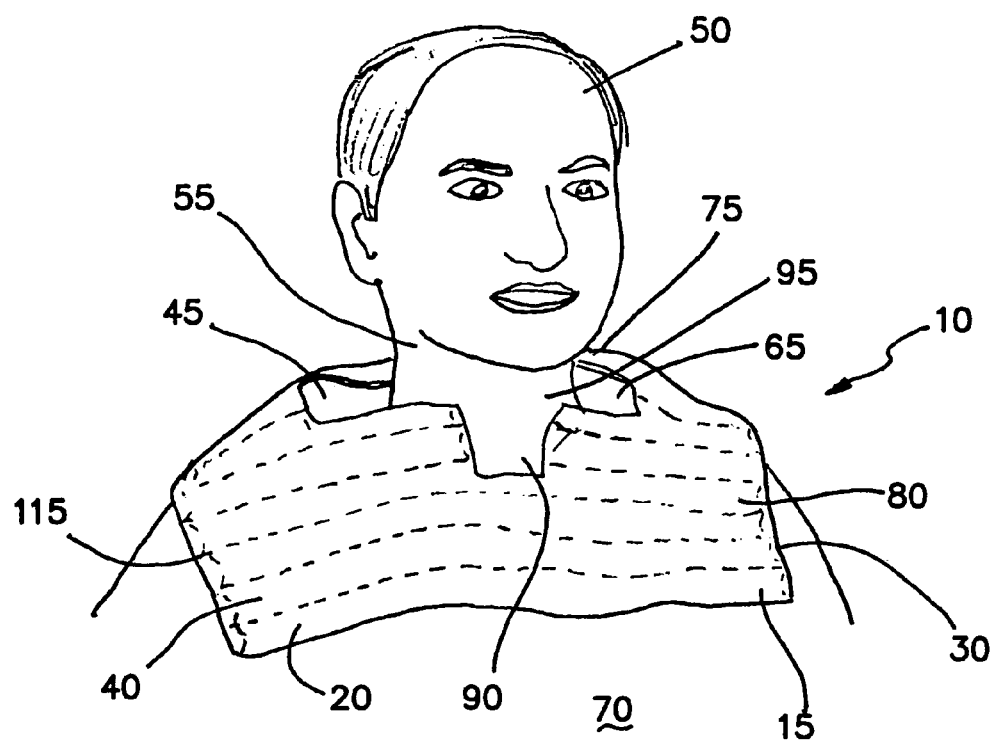
FIG. 1 is a perspective view of the preferred embodiment of the invention disposed about the neck and shoulders of a user.

(2) In a variant of the invention, the subspaces 40 are a series of tube-shaped containers 80.

(3) In another variant, the tube-shaped containers 80 are divided into substantially equal portions 87, 89 to prevent shifting of the thermal material 60 and the aromatherapy material 65.

Figure 2:
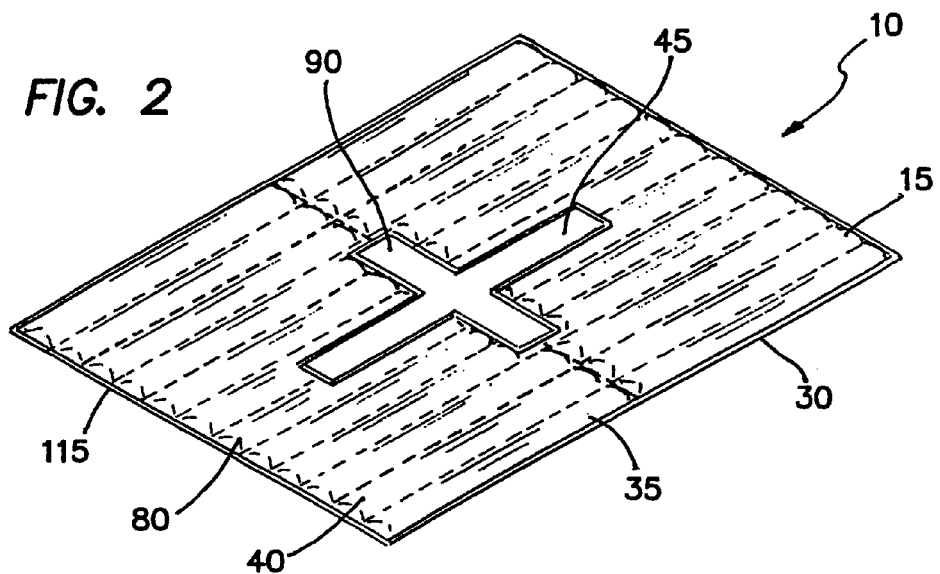
FIG. 2 is a perspective view of the of the FIG. 1 embodiment illustrating the X-shaped head opening.
Figure 3:
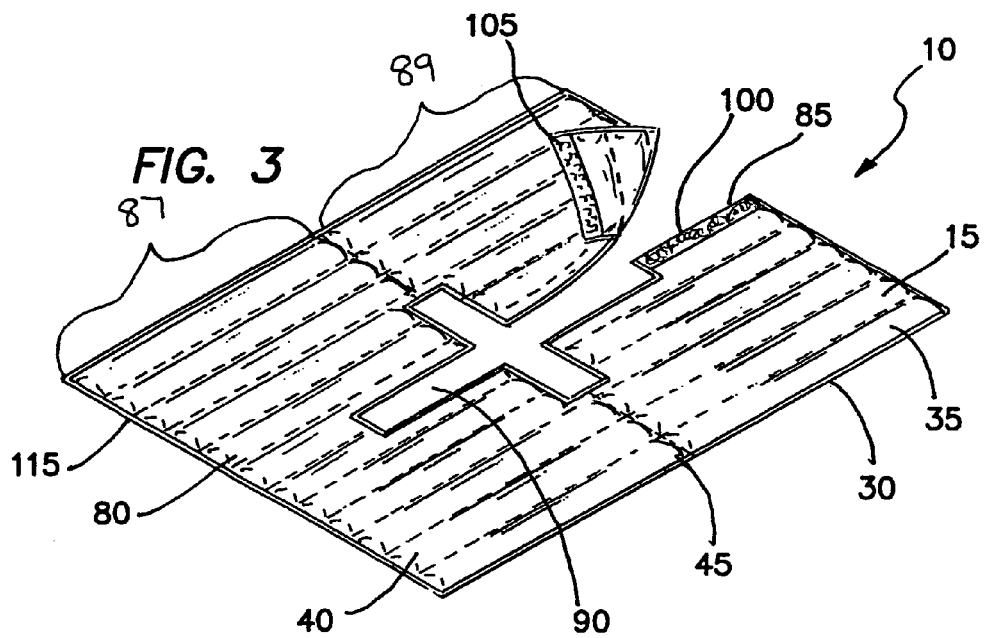
FIG. 3 is a perspective view of the of a second embodiment having a reclosable opening at one side of the X-shaped opening.

(4) In still another variant, as illustrated in FIGS. 1–3, the opening 45 is X-shaped, thereby permitting maximum contact of the herb pack 10 with the user 55 while permitting the herb pack 10 to be placed over the user's head 50.

(5) In yet another variant, as illustrated in FIG. 3, one end 85 of the X-shaped opening 90 extends to one of the outer edges 30 of the cover 15, thereby permitting the herb pack 10 to be easily placed about the wearer's neck 95.

(6) In a further variant, a fastener 100 is provided. The fastener 100 closes the open end 85 of the X-shaped opening 90 that extends to one of the outer edges 30 of the cover 15.

(7) In still a further variant, the fastener 100 is selected from the group consisting of buttons (not shown), hook and loop fasteners 105, zippers (not shown) and tie strings (not shown).

Figure 5:
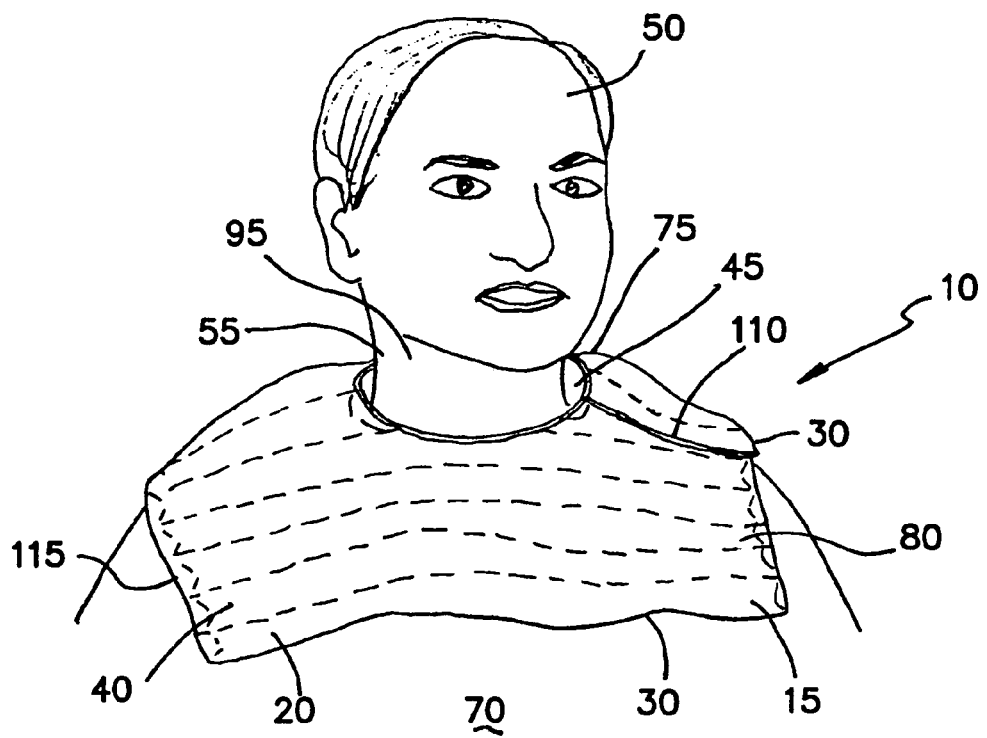
FIG. 5 is a perspective view of the of a third embodiment having a close-fitting neck opening and a reclosable slit extending from one edge of the opening to an outer edge of the herb pack disposed about the neck and shoulders of a user.
Figure 6:
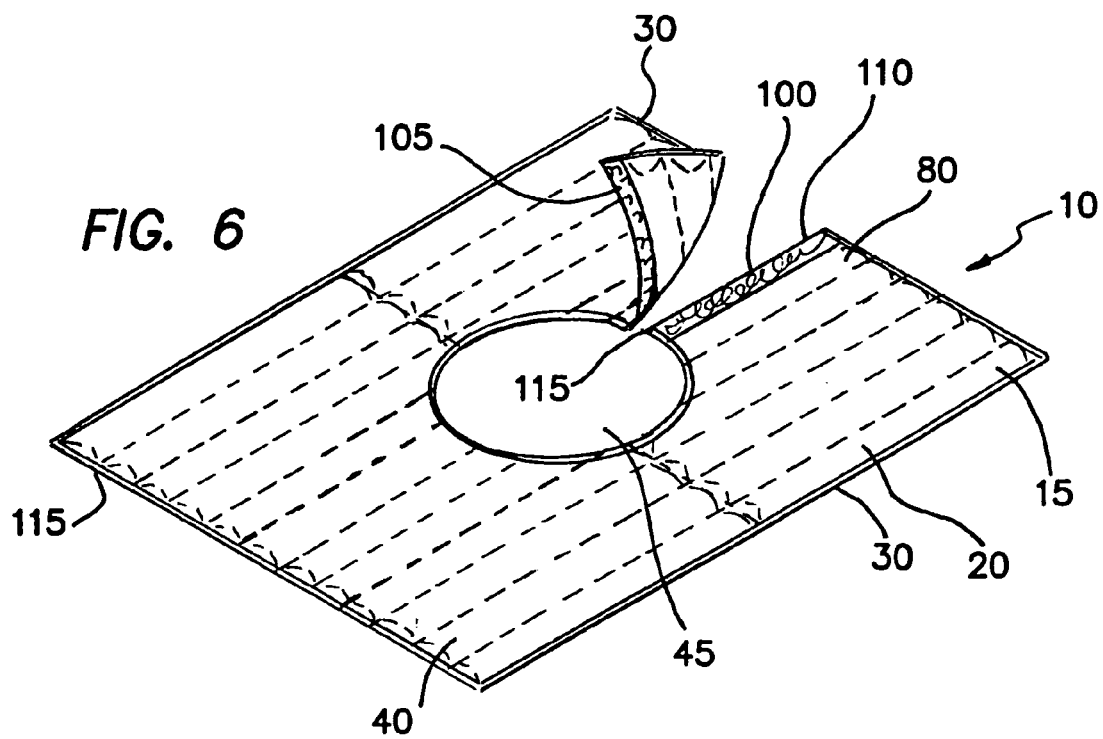
FIG. 6 is a perspective view of the FIG. 5 embodiment illustrating the reclosable slit in an open position.

(8) In yet a further variant, as illustrated in FIGS. 5 and 6, the opening 45 is sized and shaped to fit snugly about the neck 95 of the user 55 and further includes a slit 110. The slit 110 extends from an edge 115 of the opening 45 to one of the outer edges 30 of the herb pack 10.

(9) In another variant of the invention, a fastener 100 is provided. The fastener 100 closing the slit 110.

(10) In still another variant, the fastener 100 is selected from the group consisting of buttons (not shown), hook and loop fasteners 105, zippers (not shown) and tie strings (not shown).

(11) In yet another variant, the thermal reservoir materials 60 are selected from the group consisting of corn, rice, wheat, oats, barley, beans and flaxseed.

(12) In a further variant, the aromatherapy materials 65 are selected from the group consisting of cinnamon, chamomile, lemongrass, peppermint, rosemary, spearmint, valerian root, white willow, yarrow, lavender ginger and yellow dock root.

(13) In still a further variant, as illustrated in FIGS. 1–6, the subspaces 40 are closed with stitching 115.

Figure 4:
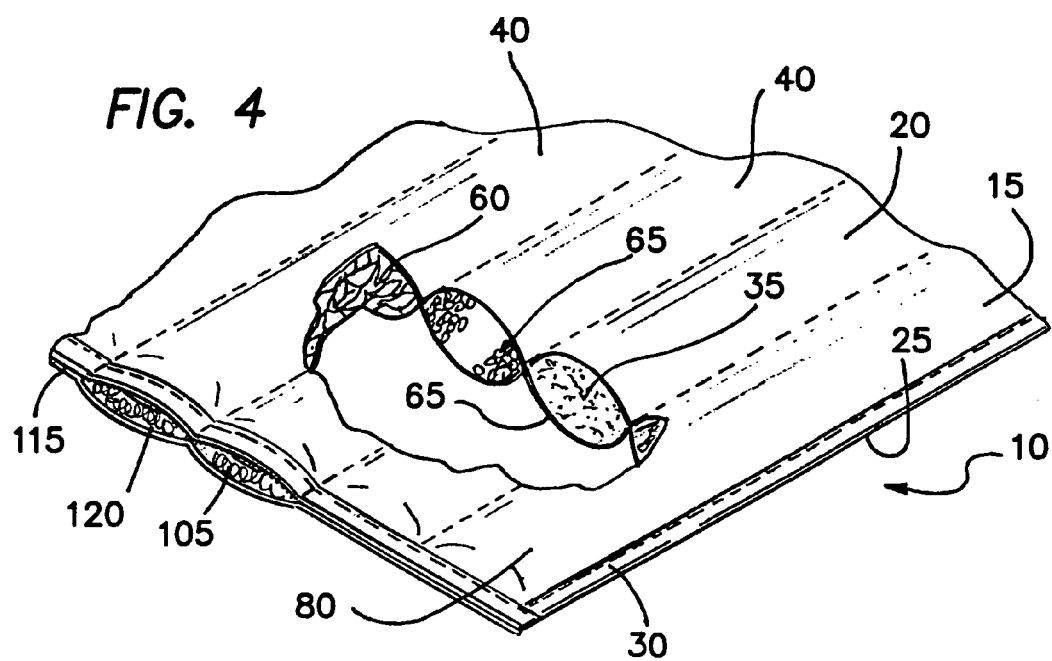
FIG. 4 is a partial cutaway perspective illustrating the tube-shaped subspaces containing thermal reservoir materials and aromatherapy materials.

(14) In yet a further variant, as illustrated in FIG. 4, the subspaces 40 have openable closures 120 to permit introduction of alternative thermal 60 and aromatherapy materials 65.

(15) In a final variant, the openable closures 120 are selected from the group consisting of hook and loop fasteners 105, zippers (not shown), buttons (not shown) and tie strings (not shown).

The aromatherapy herb pack 10 has been described with reference to particular embodiments. Other modifications and enhancements can be made without departing from the spirit and scope of the claims that follow.

The invention claimed is:

1. An aromatherapy herb pack, comprising:
    a flexible, aroma-permeable cover, said cover having an upper layer and a lower layer, said upper and lower layers being joined at outer edges thereof and defining a space therebetween, said space being divided into a plurality of subspaces;
    an X-shaped opening, said opening being centrally located in said cover and penetrating said upper, said lower layer and said subspaces and being sized and shaped to permit said cover to be placed over the head of a user;
    a quantity of thermal reservoir material;
    a quantity of aromatherapy material;
    said thermal material and said aromatherapy material being secured within said subspaces; and
    whereby, when said herb pack is heated or cooled it is placed over a head and about shoulders, chest and back of said user, thereby heating or cooling said user while providing aromatherapy benefits.

2. The aromatherapy herb pack, as described in claim 1, wherein said subspaces are a series of tube-shaped containers.

3. The aromatherapy herb pack, as described in claim 2, wherein said tube-shaped containers are divided into substantially equal portions to prevent shifting of said thermal material and said aromatherapy material.

4. The aromatherapy herb pack, as described in claim 1, wherein one end of said X-shaped opening extends to one of said outer edges of said cover, thereby permitting the herb pack to be easily placed about said wearer's neck.

5. The aromatherapy herb pack, as described in claim 4, further comprising a fastener, said fastener closing said open end of said X-shaped opening extending to one of said outer edges of said cover.

6. The aromatherapy herb pack, as described in claim 5, wherein said fastener is selected from the group consisting of:
    button, hook and loop fastener, zipper and tie string.

7. The aromatherapy herb pack, as described in claim 1, wherein said opening is sized and shaped to fit snugly about a neck of said user and further comprising a slit, said slit extending from an edge of said opening to one of said outer edges.

8. The aromatherapy herb pack, as described in claim 7, further comprising a fastener, said fastener closing said slit.

9. The aromatherapy herb pack, as described in claim 8, wherein said fastener is selected from the group consisting of:
    button, hook and loop fastener, zipper and tie string.

10. The aromatherapy herb pack, as described in claim 1, wherein said thermal reservoir material is selected from the group consisting of:
    corn, rice, wheat, oats, barley, beans and flaxseed.

11. The aromatherapy herb pack, as described in claim 1, wherein said aromatherapy material is selected from the group consisting of:
    cinnamon, chamomile, lemongrass, peppermint, rosemary, spearmint, valerian root, white willow, yarrow, lavender, ginger and yellow dock root.

12. The aromatherapy herb pack, as described in claim 1, wherein said subspaces are closed with stitching.

13. The aromatherapy herb pack, as described in claim 1, wherein said subspaces have openable closures to permit introduction of alternative thermal and aromatherapy materials.

14. The aromatherapy herb pack, as described in claim 13, wherein said openable closures are selected from the group consisting of:
    hook and loop fastener, zipper, button and tie string.

* * * * *